(12) United States Patent
Kopperschmidt et al.

(10) Patent No.: US 10,183,105 B2
(45) Date of Patent: Jan. 22, 2019

(54) APPARATUS FOR EXTRA-CORPOREAL BLOOD TREATMENT AND METHOD OF DETERMINING A BLOOD FLOW RATE FOR AN EXTRA-CORPOREAL BLOOD TREATMENT APPARATUS

(71) Applicant: Fresenius Medical Care Deutschland GmbH, Bad Homburg v.d.H. (DE)

(72) Inventors: Pascal Kopperschmidt, Dittelbrunn (DE); Wolfgang Wehmeyer, Tuebingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 548 days.

(21) Appl. No.: 13/891,768

(22) Filed: May 10, 2013

(65) Prior Publication Data

US 2013/0303964 A1 Nov. 14, 2013

Related U.S. Application Data

(60) Provisional application No. 61/645,103, filed on May 10, 2012.

(30) Foreign Application Priority Data

May 10, 2012 (DE) .................. 10 2012 009 192

(51) Int. Cl.
*A61M 37/00* (2006.01)
*A61M 1/14* (2006.01)
*A61M 1/36* (2006.01)
*A61M 1/16* (2006.01)

(52) U.S. Cl.
CPC ............ *A61M 1/14* (2013.01); *A61M 1/1601* (2014.02); *A61M 1/3621* (2013.01);
(Continued)

(58) Field of Classification Search
CPC ............ A61M 1/14; A61M 1/16; A61M 1/34; A61M 1/1603; A61M 2205/3334;
(Continued)

(56) References Cited

U.S. PATENT DOCUMENTS 5,507,723 A 4/1996 Keshaviah
5,645,531 A * 7/1997 Thompson .......... A61M 1/3621
128/DIG. 3
(Continued)

FOREIGN PATENT DOCUMENTS

DE 10 2005 025 515 A1 12/2006
DE 10 2006 045 437 A1 4/2008
(Continued)

OTHER PUBLICATIONS

International Search Report, dated Aug. 29, 2013, from corresponding International Application No. PCT/EP2013/001355.
(Continued)

*Primary Examiner* — Ariana Zimbouski
(74) *Attorney, Agent, or Firm* — Kilyk & Bowersox, P.L.L.C.

(57) ABSTRACT

An apparatus and method of determining the blood flow rate at which, in an extra-corporeal blood circuit of an extra-corporeal blood treatment apparatus, blood is pumped through the arterial blood line into the blood chamber of the dialyser and out of its blood chamber through the venous blood line is described. The method and apparatus provide for the determination of a plurality of parameters characteristic of the extra-corporeal blood treatment, with a given blood flow rate being determined in each case as a function of one of the characteristic parameters. A blood flow rate which is preset for the blood treatment is selected from the plurality of blood flow rates determined on the basis of the characteristic parameters. The blood flow rate to be preset is
(Continued)

selected on the basis of a preset algorithm which may be implemented in software installed on a data processing unit or in hardware.

8 Claims, 2 Drawing Sheets

(52) U.S. Cl.
CPC ........ *A61M 1/3626* (2013.01); *A61M 1/3639* (2013.01); *A61M 2205/3334* (2013.01); *A61M 2205/50* (2013.01)

(58) Field of Classification Search
CPC .............. A61M 1/1601; A61M 1/3621; A61M 1/3626; A61M 1/3639
See application file for complete search history.

(56) References Cited

U.S. PATENT DOCUMENTS

| | | | |
|---|---|---|---|
| 5,744,031 A * | 4/1998 | Bene | 210/321.71 |
| 6,200,485 B1 | 3/2001 | Kitaevich et al. | |
| 2005/0202397 A1 * | 9/2005 | Zhang | A61M 1/3639 435/4 |
| 2009/0205426 A1 * | 8/2009 | Balschat et al. | 73/599 |
| 2010/0168641 A1 | 7/2010 | O'Mahony et al. | |

FOREIGN PATENT DOCUMENTS

| | | |
|---|---|---|
| DE | 10 2007 026 010 A1 | 12/2008 |
| DE | 10 2011 102 872 A1 | 12/2012 |
| EP | 0240101 A2 | 10/1987 |
| EP | 0834329 A1 | 4/1998 |
| EP | 0 845 273 A1 | 6/1998 |
| EP | 2 383 004 A1 | 11/2011 |
| WO | 2006/128520 A1 | 12/2006 |

OTHER PUBLICATIONS

International Preliminary Report on Patentability, dated Nov. 11, 2014, from corresponding International Application No. PCT/EP2013/001355.

* cited by examiner

APPARATUS FOR EXTRA-CORPOREAL BLOOD TREATMENT AND METHOD OF DETERMINING A BLOOD FLOW RATE FOR AN EXTRA-CORPOREAL BLOOD TREATMENT APPARATUS

CROSS REFERENCE TO RELATED APPLICATIONS

The present application claims priority to Application No. DE 10 2012 009 192.3, filed in the Federal Republic of Germany on May 10, 2012, and claims priority to U.S. Provisional Application Ser. No. 61/645,103, filed on May 10, 2012, the contents of which are hereby incorporated herein in their entirety by reference thereto.

FIELD OF INVENTION

The present invention relates to an apparatus for extra-corporeal blood treatment in which, in an extra-corporeal blood circuit, blood flows through an arterial blood line into the blood chamber of a dialyser which is divided into the blood chamber and a dialysis-fluid chamber by a semi-permeable membrane, and flows out of the blood chamber through a venous blood line. As well as this, the present invention also relates to a method of determining the blood flow rate at which, in the extra-corporeal blood circuit of an extra-corporeal blood treatment apparatus, blood is pumped into the blood chamber of the dialyser through the arterial blood line and out of its blood chamber through the venous blood line.

BACKGROUND INFORMATION

There are various known methods of treating blood extra-corporeally such for example as haemodialysis, haemofiltration and the combination of these two methods which is referred to as haemodiafiltration. During haemodialysis treatment, the patient's blood and a dialysis fluid flow across the semi-permeable membrane which divides the dialyser into the blood and dialysis-fluid chambers, preferably in counter-current and each at a preset flow rate.

To optimise the methods of blood treatment, it is known for parameters characteristic of the blood treatment to be determined. These characteristic parameters include in particular the parameters which define the metabolic performance of the dialyser.

The metabolic performance of the dialyser can be defined by clearance, which, for a given substance, means that virtual volume of blood which, per minute, is completely freed of the substance in question by the dialyser. Dialysance is a further term for use in determining the performance of the dialyser and in its case account is also taken of the concentration in the dialysis fluid of the substance involved in the metabolic exchange in the dialyser.

Clearance or dialysance depends in turn, to crucial degree, on the preset blood flow rate at which the patient's blood flows through the blood chamber of the dialyser. As the blood flow rate increases so too does the clearance in this case. The blood treatment should therefore take place at as high a blood flow rate as possible. However, in practice there are found to be limits on how far the blood flow rate can be increased.

An upper limit on the blood flow rate is set by the vascular access, which puts a limit on the arterial inflow pressure and venous return pressure in the blood lines. An increase in the blood flow rate at which the blood pump pumps the blood through the blood lines results in an increase in the suction pressure from the blood pump, which may cause the vessel to collapse or the puncture needle to be sucked against the wall of the vessel. If this happens, an arterial pressure alarm is triggered. The limiting values for the blood flow rate differ from patient to patient as a function of the characteristics of the vascular access. Even on the same patient different limiting values arise for the blood flow rate because, for example, recently fitted shunts (arterio-venous fistulas) are generally still relatively unstable and will not stand excessively high pressures. Current maximum values for the inflow pressures are in the range from −200 mmHg to −150 mmHg, and for the return pressures figures of up to +150 mmHg to +200 mmHg are tolerated. The level of the blood flow rate is also of crucial importance in the case of the puncture needles because needles of small diameter set up a greater resistance to flow than ones of a large diameter.

To date, the blood flow rate has been set manually with due allowance for the preset parameters. What is often habitually set is a value which has proved satisfactory in practice, such for example as 300 ml/min, 350 ml/min or 400 ml/min, even though the blood and the patient's physiology would, fundamentally, allow values different from this to be set.

SUMMARY

An object underlying the present invention is to provide an apparatus for extra-corporeal blood treatment which makes provision for the blood flow rate which is to be preset to be optimised for the purpose of maximising the metabolic performance of the dialyser. As well as this, an object underlying the invention is also to specify a method of determining the blood flow rate to be preset for the blood treatment at which the metabolic performance of the dialyser can be optimised.

The method according to the present invention and the apparatus according to the present invention make provision for the determination of at least one parameter, but preferably a plurality of parameters, characteristic of the extra-corporeal blood treatment and in particular of the extra-corporeal blood circuit, a given blood flow rate being determined in each case as a function of the one characteristic parameter or preferably of one of the characteristic parameters. The basic principle of the present invention lies in selecting from, preferably, the plurality of blood flow rates which are determined on the basis of the characteristic parameters a blood flow rate which is preset for the blood treatment. The blood flow rate to be preset is selected in this case on the basis of a preset algorithm which may be implemented in software installed on a data processing unit or in hardware. What is meant by an algorithm in this case is any unambiguous set of instructions which allows the blood flow rate to be selected automatically.

In the event of the method according to the present invention and apparatus according to the present invention making provision only for one parameter characteristic of the extra-corporeal blood treatment to be determined, the blood flow rate to be preset is determined on the basis of a preset algorithm as a function of this characteristic parameter. Consequently, the blood flow rate is not preset manually but is set automatically.

In the apparatus according to the present invention for extra-corporeal blood treatment, the arrangement for presetting the blood flow rate is so designed that automatic selection of the given blood flow rate takes place on the basis of the preset criterion for selection. The arrangement for presetting the blood flow rate has a separate data processing unit which is programmed in such a way that the blood flow rate at which the means for pumping blood in the extra-corporeal blood circuit, such as for example the blood pump arranged in the arterial blood line, are operated is selected on the basis of the preset algorithm.

The arrangements for determining the blood flow rates as a function of the characteristic parameters may themselves be regulating arrangements which regulate the blood flow rate as a function of the parameters concerned. In this case the individual regulating arrangements give the arrangement for presetting the blood flow rate recommended blood flow rates on the basis of the characteristic parameters, which characteristic parameters are monitored independently of one another. The arrangement for presetting the blood flow rate may itself, in turn, be a regulating arrangement, which then regulates the blood flow rate as a function of the characteristic parameter concerned on the basis of which the arrangement made the selection.

The algorithm for selecting the blood flow rate to be preset for the blood treatment may make provision for different criteria for selection. Preferably, the blood flow rate which is selected from the recommended blood flow rates is that at which a blood treatment can be carried out with great safety. In practice, the criterion for selection will therefore be to select the lowest value from the recommended blood flow rates.

In a preferred exemplary embodiment of the present invention, what play a part in the selection of the optimum blood flow rate are not only the blood flow rates which are determined dynamically as a function of the characteristic parameters but also preset static blood flow rates which preset a maximum value and/or a minimum value for the blood flow rate. It is possible in this way for maximum and/or minimum values for the blood flow rate to be taken into account when the optimum blood flow rate is being selected. This further increases the safety of the blood treatment.

It is of fundamental importance to the present invention what characteristic parameters are looked at for the purpose of determining the individual blood flow rates. These are in particular those parameters which bear a close relationship to changes in the blood flow rate. Provision is made in particular for monitoring the clearance which defines the metabolic performance of the dialyser and/or for monitoring the arterial pressure in the arterial blood line and/or for monitoring the venous pressure in the venous blood line. The determining of these parameters characteristic of the blood treatment is familiar to the person skilled in the art. Arrangements for determining these parameters are part of the prior art.

A further exemplary embodiment which is a particular preference also makes provision for the determination of a parameter characteristic of the number of micro-bubbles present in the blood, because a certain volume of micro-bubbles dissolved in the blood may not be exceeded. An arrangement for determining a parameter of this kind is also part of the prior art. The formation of micro-bubbles (cavitation) may take place as a result of negative arterial pressure. Leaks in the system of blood tubing combined with a blood pressure in the blood tubing which is negative relative to the external pressure may also result in the formation of micro-bubbles.

In a further exemplary embodiment which is a particular preference, the arrangement for presetting the blood flow rate presets as a starting value for the blood treatment a blood flow rate at which a preceding blood treatment carried out on the same patient came to an end. Basically, it is however also possible to preset as a starting value a blood flow rate at which a preceding blood treatment began. However, the presetting of the blood flow rate which existed at the end of the blood treatment affords increased safety for the patient because the blood flow rate generally goes down over the course of a treatment due to the thickening of the blood.

The apparatus according to the present invention and the method according to the present invention make it possible for the volume of blood treated within a preset treatment time to be maximised without it being possible for the blood or the blood vessels to be damaged. The blood flow rate can be matched dynamically to varying conditions in this case. All in all, the cleansing performance for large and small molecules is optimised. With the apparatus according to the present invention and the method according to the present invention it is also possible for the number of alarms, and in particular pressure alarms, during the treatment to be minimised. The selection of the optimum blood flow rate is preferably indicated to the medical personnel. For example, the personnel may be able to see on an indicator unit which of the determined characteristic parameters the selection of the blood flow rate was based on. This makes it possible for variations at the vascular access to be observed and an assessment to be made of the quality of the puncture, thus enabling long-term trends to be revealed relating to the volume of blood treated.

In what follows, an exemplary embodiment of the present invention is explained in detail with reference to the accompanying drawings.

DETAILED DESCRIPTION

Figure 1:
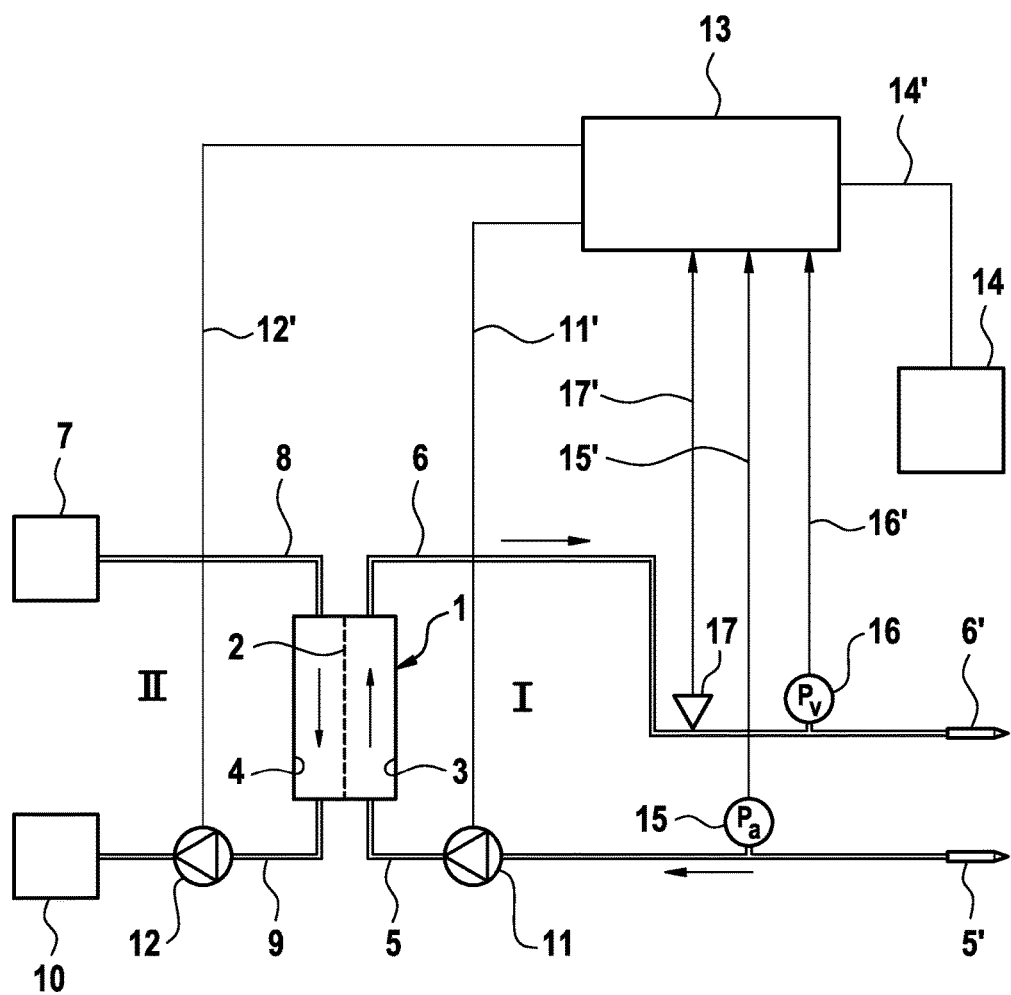
FIG. 1 is a highly simplified schematic view of the principal components of the blood treatment apparatus according to the present invention including the arrangement for presetting the blood flow rate.

The blood treatment apparatus, such as a haemodialysis apparatus for example, has a dialyser 1 which is divided into a blood chamber 3 and a dialysis-fluid chamber 4 by a semi-permeable membrane 2. The inlet to the blood chamber 3 is connected to one end of a blood infeed line 5 while the outlet from the blood chamber 3 is connected to one end of a blood outfeed line 6. The other ends of the blood infeed and outfeed lines 5, 6 are connected to arterial and venous needles 5', 6' respectively, which are connected to the vascular access (not shown) to the patient. Together with the blood chamber 3 of the dialyser 1, the blood infeed and outfeed lines 5, 6 form the extra-corporeal blood circuit I of the blood treatment apparatus.

The dialysis fluid system II of the blood treatment apparatus comprises an arrangement 7 for preparing the dialysis fluid, from which there is an outgoing dialysis-fluid infeed line 8 which runs to the dialysis-fluid chamber 4. From the dialysis-fluid chamber 4 there is an outgoing dialysis-fluid outfeed line 9 which runs to a discharge 10.

Arranged in the blood infeed line 5 is a blood pump 11 while a dialysis-fluid pump 12 is arranged in the dialysis-fluid outfeed line 9. During the blood treatment the blood pump 11 pumps blood from the patient into the blood chamber 3 through the arterial blood line 5 and out of the blood chamber 3 through the venous blood line 6 to the patient.

The blood treatment apparatus comprises a central control and calculating unit 13 which is connected by control lines 11' and 12' respectively to the blood pump 11 and the dialysis-fluid pump 12 to enable the blood and dialysis-fluid flow rates respectively to be set.

During the blood treatment, a variety of parameters characteristic of the blood treatment are preferably monitored. For this purpose, the blood treatment apparatus preferably has a plurality of arrangements by each of which a characteristic parameter is determined. These arrangements are only shown schematically in FIG. 1. The arrangements shown are only intended to serve as examples. Basically, it is however also possible for only one characteristic parameter to be monitored.

The blood treatment apparatus has an arrangement 14 for determining the clearance K or the change ΔK in the clearance when there is an increase in the blood flow rate $Q_B(t)$. A method and an arrangement for determining clearance are described in European Application No. EP 0 845 273 A1 for example. The clearance K rises as the blood flow rate increases. However, as a rule the rise is not linear because, if there is an increased extra-corporeal blood flow there is also increased recirculation of the blood through the patient's fistula. Because of this, the clearance moves towards a limiting value at an increased blood flow rate.

As well as the arrangement for determining clearance, the blood treatment apparatus also has an arrangement 15 for determining the arterial pressure $P_a(t)$ in the arterial blood line 5 and an arrangement 16 for determining the venous pressure $P_v(t)$ in the venous blood line 6. The arterial and venous pressures may be monitored by suitable sensors in the apparatus. An arrangement for measuring arterial and venous pressures is described for example in European Application No. EP 2 383 004 A1.

Because the blood is drawn into the arterial blood line 5 by the blood pump 11 by suction, the blood is subject to a pressure below atmospheric, which may result in gas being released from the blood. This produces micro-bubbles dissolved in the blood which cannot be completely removed from the blood and which are therefore fed back again to the patient venously. It is true that the patient can safely deal with a certain volume of dissolved micro-bubbles. However, if a limiting value for the built-up volume of infused micro-bubbles MES(t) is exceeded, there is a danger of the patient being put at risk by an embolism. The blood treatment apparatus therefore preferably also has an arrangement 17 to determine a parameter which correlates with the number or volume of micro-bubbles present in the blood. An arrangement of this kind is described for example in International Patent Publication No. WO 2006/128520 A1. The frequency of occurrence of embolic events can be analysed with this arrangement.

The central calculating and control unit 13 of the blood treatment apparatus will be described in detail below by reference to FIG. 2.

Via signal lines 14', 15', 16', 17' which are connected to the corresponding arrangements 14, 15, 16, 17 for determining the characteristic parameters, the calculating and control unit 13 receives the parameters which are determined.

For each of the characteristic parameters, the calculating and control unit 13 has an arrangement which determines a blood flow rate $Q_{Ba}(t)$ as a function of the characteristic parameter which is determined. These arrangements may be regulating arrangements, in which case the characteristic parameter is the regulated variable.

Figure 2:
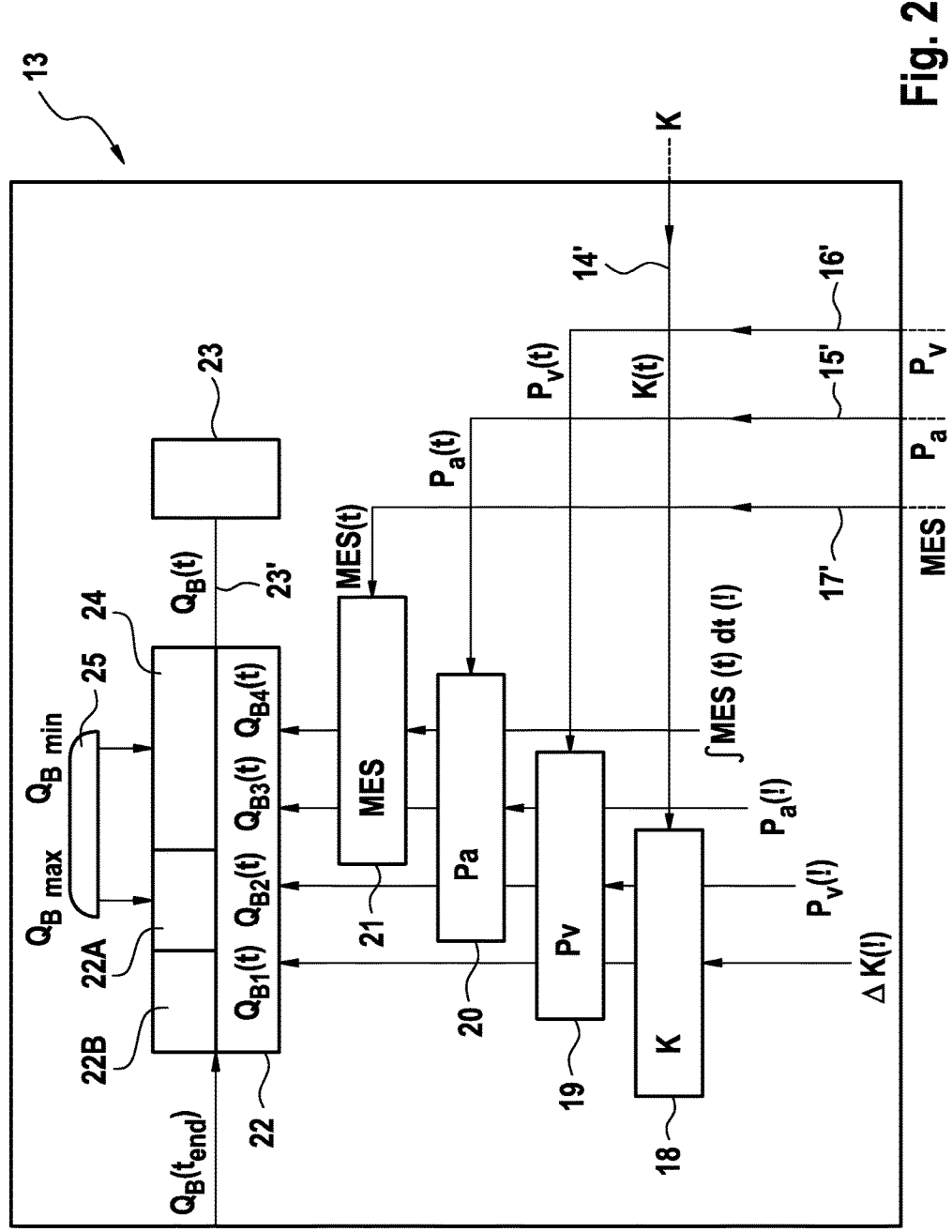
FIG. 2 is a highly simplified schematic view of the central calculating and control unit of the blood treatment apparatus according to the present invention.

The individual arrangements are shown in FIG. 2. The first regulating arrangement 18 determines a first blood flow rate $Q_{B1}(t)$ as a function of the clearance(t) (K(t)), the second regulating arrangement 19 determines a second blood flow rate $Q_{B2}(t)$ as a function of the venous pressure $P_v(t)$, the third regulating arrangement 20 determines a third blood flow rate $Q_{B3}(t)$ as a function of the arterial pressure $P_a(t)$, and the fourth regulating arrangement 21 determines a fourth blood flow rate $Q_{B4}(t)$ as a function of the parameter MES(t) characteristic of the number of micro-bubbles. In doing so, the regulating arrangements 18 to 21 compare the actual values which are measured with the preset desired values K(!), $P_v(!)$, $P_a(!)$, ∫MES(t)dt(!). Regulating arrangements of this kind are part of the prior art.

The number of regulating arrangements (18 to 21) shown in FIG. 2 is merely an example. One exemplary embodiment may comprise only one regulating arrangement, corresponding to one characteristic parameter. Another exemplary embodiment may comprise as many regulating arrangements as desired corresponding to as many characteristic parameters as desired.

The calculating and control unit 13 also has an arrangement 22 for presetting one blood flow rate $Q_B(t)$ from the blood flow rates $Q_{Bn}(t)$ which are suggested by the individual regulating arrangements 18 to 21. In what follows, the arrangement 22 for presetting a blood flow rate $Q_B(t)$ will also be referred to as a selecting arrangement. The selection is made by following a given algorithm.

The selecting arrangement 22 has a data processing unit 22A on which a data processing program runs. The data processing unit 22A may be a self-contained data processing unit or may be part of a data processing unit (microprocessor) which belongs to the central calculating and control unit 13. The data processing unit is programmed in such a way that the selection of the blood flow rate is performed by following the algorithm.

When the blood flow rate is being selected, it is not only the dynamic parameters $Q_{B1}(t)$ to $Q_{B4}(t)$ which are taken into account but also two static parameters which are preset by an arrangement 25. The arrangement 25 for presetting the static parameters may be an input unit. These parameters are a maximum value $Q_{B\ max}$ and a minimum value $Q_{B\ min}$ for the blood flow rate $Q_B(t)$.

In a preferred exemplary embodiment, the selecting arrangement 22 compares the suggested blood flow rates $Q_{Bn}(t)$ and determines that blood flow rate $Q_B(t)$ which represents the lowest of the blood flow rates. The value of this blood flow rate is then compared with the maximum value $Q_{B\ max}$ and minimum value $Q_{B\ min}$. If the value $Q_B(t)$ is more than the minimum value $Q_{B\ min}$ and less than the maximum value $Q_{B\ max}$, the arrangement 22 presets the value $Q_B(t)$ as the blood flow rate. This value changes over the course of the blood treatment as a function of the characteristic parameters which are measured.

Thus, during the blood treatment, the regulation of the blood flow rate takes place on the basis of the preset algorithm as a function of one or more of the characteristic parameters. It is thus possible for the regulation to be performed with for example the arterial and/or venous pressures $P_a(t)$, $P_v(t)$ as controlling variables or a controlling variable in one interval of time during the blood treatment and with for example the clearance(t) as a controlling variable in another interval of time. Consequently, the controlling variables may alter continuously.

In the present exemplary embodiment, the regulating arrangement 21 analyzes the frequency of occurrence of embolic events and regulates the blood flow rate $Q_B(t)$ in such a way that the frequency of embolic events is below a given limiting value. The regulating arrangement 20 regulates the blood flow rate $Q_B(t)$ in such a way that the desired value $P_a(!)$ set for the arterial pressure $P_a(t)$ is achieved, while the regulating arrangement 19 regulates the venous pressure $P_v(t)$ in such a way that the actual value $P_v(t)$ corresponds to the desired value $P_v(!)$. The regulating arrangement 18 attempts to limit the effect of the recirculation between the arterial and venous accesses which increases with an increase in the blood flow rate.

As well as this, there is also provided a indicator unit 23 which is connected to the arrangement 22 for selecting the blood flow rate $Q_B(t)$ by a signal line 23'. On the indicator unit 23 it is indicated to the medical personnel which of the characteristic parameters is controlling the regulation at the time. The medical personnel is thus able to monitor during the blood treatment whether the regulation is taking place on the basis of, for example, the arterial and/or venous pressure $P_{a,v}(t)$ or the clearance or the embolic events MES. The indication on the indicator unit 23 can be given by the known visual and/or acoustic means.

At the beginning of the blood treatment, the medical personnel may preset a fixed value for the blood flow rate $Q_B(t)$, which then changes automatically over the course of the blood treatment. However, a preferred exemplary embodiment makes provision for the data processing unit 22 to have a memory 24 in which there is stored, as a starting value for a subsequent blood treatment on a patient, the patient-specific value of the blood flow rate which existed at the end of a preceding blood treatment on the patient. This value is read out of the memory 24 at the beginning of the blood treatment and is preset as a starting value for the fresh treatment. Stored in the memory 24 are a plurality of values for a plurality of patients which can be called up at the beginning of their individual blood treatments.

What is claimed is:

1. A method of determining a preset blood flow rate at which, in an extra-corporeal blood circuit, blood is pumped by a blood pump for pumping blood through an arterial blood line into a blood chamber of a dialyser that is divided into the blood chamber and a dialysis-fluid chamber by a semi-permeable membrane, and out of the blood chamber through a venous blood line, the dialysis-fluid chamber being part of a dialysis fluid system, the method comprising:
   determining values for four parameter characteristics of the extra-corporeal blood treatment, the four parameter characteristics comprising
      clearance of the dialyzer,
      arterial pressure in the arterial blood line,
      venous pressure in the venous blood line, and
      the number or volume of micro-bubbles present in the blood in the venous blood line;
   determining more than one suggested blood flow rate by comparing a respective value of each of the four parameter characteristics determined with a respective preset desired value, to determine a respective one of the more than one suggested blood flow rates as a function of the respective comparison, the respective values of the four parameter characteristics determined comprising the arterial pressure in the arterial blood line, the venous pressure in the venous blood line, clearance of the dialyzer, and the number or volume of micro-bubbles present in the blood in the venous blood line; and
   selecting, with a calculating and control unit, one preset blood flow rate of the more than one suggested blood flow rates, at which the blood pump for pumping blood in the extra-corporeal blood circuit is operated, the calculating and control unit comprising a micro-processor on which a data processing program runs, the micro-processor being programmed to follow a preset algorithm for selecting the one preset blood rate thus causing blood to flow through the extra-corporeal blood circuit at the one preset blood flow rate, the calculating and control unit being connected to the blood pump by a blood pump control line, wherein, by following the preset algorithm, the micro-processor is programmed to select the lowest preset blood flow rate of the suggested blood flow rates, compare the selected lowest preset blood flow rate with a preset minimum value for blood flow rate, and cause blood to flow through the extra-corporeal blood circuit at the selected lowest preset blood flow rate only if the selected lowest preset blood flow rate is more than the preset minimum value.

2. The method according to claim 1, further comprising:
   presetting two static parameters that are a preset maximum value and the preset minimum value for blood flow rate, wherein the micro-processor selects the lowest preset blood flow rate, of the suggested blood flow rates, that
   does not exceed the preset maximum value and is not lower than the preset minimum value.

3. The method according to claim 1, further comprising:
   selecting a preset blood flow rate from a preceding blood treatment, which is stored in a memory unit, as a starting value for a subsequent blood treatment, at a beginning of the subsequent blood treatment.

4. The method according to claim 1, wherein the selecting a preset blood flow rate comprises selecting on the basis of the preset algorithm and on the basis of the suggested blood flow rate determined by comparing the determined value of arterial pressure in the arterial blood line with the respective preset desired value of arterial pressure in the arterial blood line.

5. The method according to claim 1, wherein the selecting a preset blood flow rate comprises selecting on the basis of the preset algorithm and on the basis of the suggested blood flow rate determined by comparing the determined value of venous pressure in the venous blood line with the respective preset desired value of venous pressure in the venous blood line.

6. The method according to claim 1, wherein the selecting a preset blood flow rate comprises selecting on the basis of the preset algorithm and on the basis of the suggested blood flow rate determined by comparing the determined value of clearance of the dialyzer with the respective preset desired value of clearance of the dialyzer.

7. The method according to claim 1, wherein the selecting a preset blood flow rate comprises selecting on the basis of the preset algorithm and on the basis of the suggested blood flow rate determined by comparing the determined value of the number or volume of micro-bubbles present in the blood in the venous blood line with the respective preset desired value of the number or volume of micro-bubbles present in the blood in the venous blood line.

8. The method according to claim 1, further comprising:
   visually or acoustically indicating the value of the parameter characteristic of the extra-corporeal blood treatment, on the basis of which the preset blood flow rate is selected.

* * * * *